(12) United States Patent
Stålberg

(10) Patent No.: US 6,960,542 B2
(45) Date of Patent: Nov. 1, 2005

(54) METHOD FOR PREPARATION OF TEST BODIES

(75) Inventor: Sven-Olof Stålberg, Trollhätan (SE)

(73) Assignee: Volvo Aero Corporation, Trollhättan (SE)

( * ) Notice: Subject to any disclaimer, the term of this patent is extended or adjusted under 35 U.S.C. 154(b) by 249 days.

(21) Appl. No.: 10/351,445

(22) Filed: Jan. 27, 2003

(65) Prior Publication Data

US 2003/0124274 A1    Jul. 3, 2003

Related U.S. Application Data

(63) Continuation of application No. 09/647,746, filed as application No. PCT/SE00/00280 on Feb. 11, 2000, now Pat. No. 6,547,998.

(30) Foreign Application Priority Data

Feb. 17, 1999    (SE) .................................... 9900538

(51) Int. Cl.$^7$ ............................................. B32B 27/04
(52) U.S. Cl. ..................... 442/43; 442/58; 428/306.6; 428/542.8; 428/543
(58) Field of Search ................................ 442/2, 43, 50, 442/58; 428/542.8, 543, 304.4, 306.6, 311.11

(56) References Cited

U.S. PATENT DOCUMENTS

| | | |
|---|---|---|
| 3,379,603 A | 4/1968 | Barnette |
| 3,596,317 A | 8/1971 | Nicholson |
| 3,733,768 A | 5/1973 | Carls et al. |
| 3,761,554 A | 9/1973 | Barnette |
| 3,763,611 A | 10/1973 | Duhring et al. |
| 3,886,248 A | 5/1975 | Nicholson |
| 3,994,763 A | 11/1976 | Sheath et al. |
| 4,419,314 A | 12/1983 | Bush |
| 4,623,500 A | 11/1986 | Nelson et al. |
| 4,655,700 A | 4/1987 | Ahmed |
| 4,681,718 A | 7/1987 | Oldham |
| 4,724,110 A | 2/1988 | Arnold |
| 5,269,999 A | 12/1993 | Smesny |
| 5,968,436 A | 10/1999 | Takezaki |

FOREIGN PATENT DOCUMENTS

| | | |
|---|---|---|
| DE | 4400 815 | 7/1995 |
| GB | 214 4366 | 3/1985 |
| JP | 55-027975 | 2/1980 |

*Primary Examiner*—Terrel Morris
*Assistant Examiner*—Arden B. Sperty
(74) *Attorney, Agent, or Firm*—Dickstein Shapiro Morin & Oshinsky LLP

(57) ABSTRACT

The invention relates to a method for preparation of test bodies for analysis of porous, preferably thermally sprayed, surface layers, which are incorporated by casting in plastic. The method according to the invention is carried out by placing one or more test pieces of the surface layer in a mold introduced into a vacuum chamber, the pressure of which is lowered, pouring a ready-mixed, liquid casting resin into the mold containing the test pieces, again letting the air into the chamber, lifting the test pieces out of the casting resin and allowing the excess resin to drip from the test pieces. After that, they are placed in a mold cavity together with the test pieces with a pulverized resin, and applying pressure and heat to the mold cavity for a predetermined period of time, whereupon the test body is ready to be taken out and lapped.

6 Claims, 1 Drawing Sheet

METHOD FOR PREPARATION OF TEST BODIES

This application is a continuation of application Ser. No. 09/647,746 filed Oct. 4, 2000 now U.S. Pat. No. 6,547,998 which is a 371 of PCT/SE00/00280, filed Feb. 11, 2000, the disclosure of which is incorporated herein by reference.

BACKGROUND OF THE INVENTION

The invention relates to a method for preparation of test bodies for analysis of porous, preferably thermally sprayed, surface layers which are incorporated by casting in plastic.

To be able to analyze thermally sprayed surface layers, so called test bodies have to be produced, which are lapped and examined and evaluated with the use of a microscope with regard to the structure of the surface layer. It is when the test body is lapped that the problem arises in that the surface layer is "smeared out", which will give a false structure.

There are two known methods for incorporating by casting of test bodies, viz. on one hand a cold casting method and on the other hand a warm casting method, which will be described below.

In the cold casting method, test bodies are produced by incorporating by casting a test piece under vacuum in a specific two-component resin of epoxy type with very good penetration ability into porous layers, i.e. the surface of the test pieces are wetted very well. Since the epoxy resin will fill out all pin-holes and voids in the surface layer, said surface layer can be lapped after curing the epoxy resin with a very good result without any smearing of said surface layer, whereby a true structure is obtained which can be evaluated with use of a microscope.

This method suffers from the drawbacks that on one hand the curing time for the epoxy system used at room temperature amounts to several hours and that on the other hand the epoxy resin used is very expensive, which means that the costs can be very high at a large number of tests.

In the other method, i.e. the hot casting method, test bodies are produced in the way that a sample of the surface layer is incorporated by casting in a pulverized phenolic plastic, preferably bakelite, at a pressure of about 5–15 kN and a temperature of about 150° C. in a so called Prontopress. This method has the advantage that the incorporation by casting is very fast, about 15 minutes, and that the cost per body is very low. However, the drawback is that the bakelite does not penetrate into the pin-holes and voids in the porous surface layer, whereby the result of the lapping of the surface layer is non-useable, since there is a great risk for "smearing" of the surface layer, which will produce a false structure.

SUMMARY OF THE INVENTION

The object of the invention is to reduce the drawbacks of the above-mentioned methods. This is achieved according to the invention by: (1) placing one or more test pieces of the surface layer in a mold introduced into a vacuum chamber, the pressure of which is lowered; (2) pouring a ready-mixed, liquid casting resin into the mold containing the test pieces; (3) again letting the air into the chamber; (4) lifting the test pieces out of the casting resin and allowing excess of casting resin to drip from the test pieces, and after that, placing the test pieces in a mold cavity of a hot molding press; (5) filling said mold cavity together with the test pieces with a pulverized resin; and (6) applying pressure and heat to the mold cavity for a predetermined period of time, whereupon the test body is ready to be taken out and lapped.

DETAILED DESCRIPTION OF THE INVENTION

Figure 1:
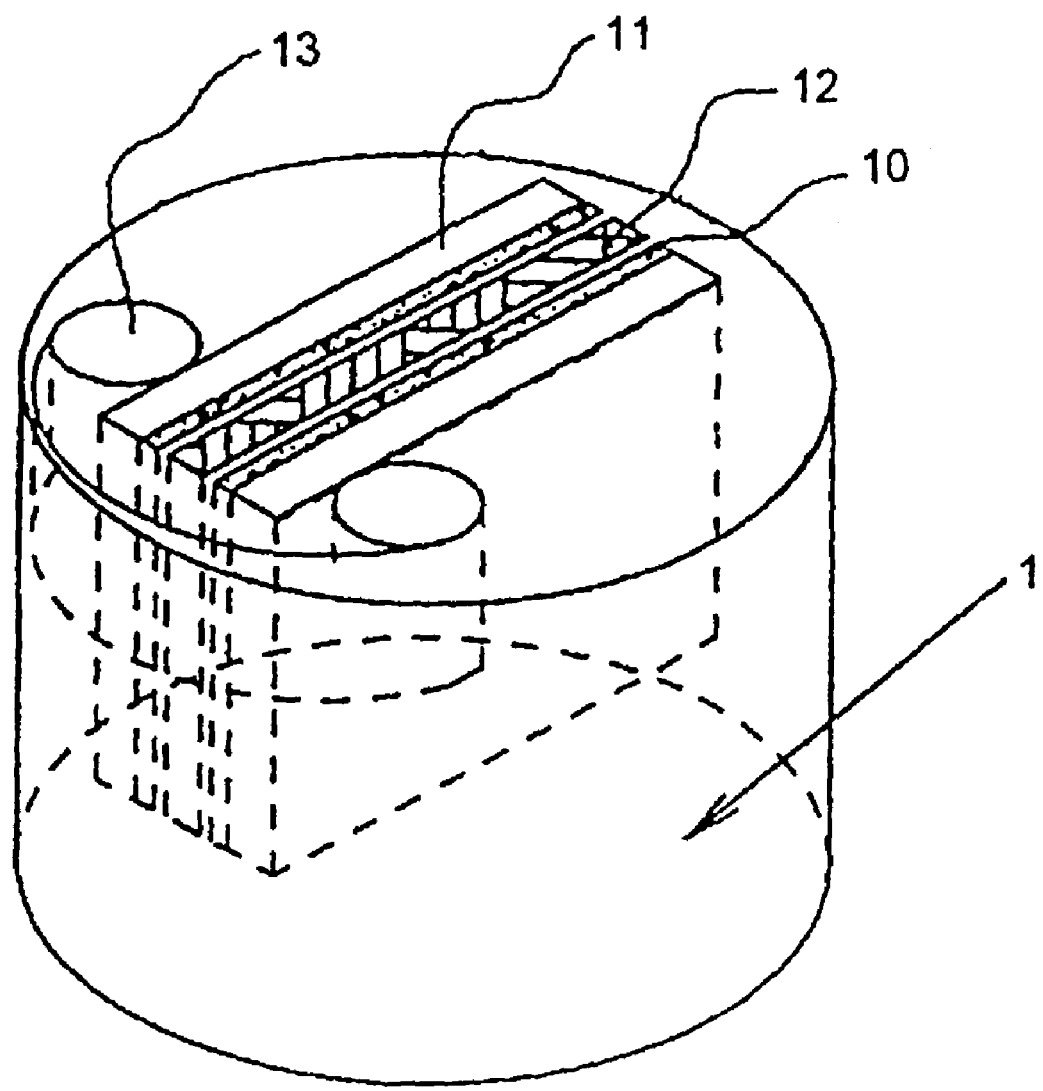
FIG. 1 illustrates an exemplary ready-made test body with sprayed layers incorporated by the casting method under an embodiment of the present invention.

A non-limiting embodiment of the invention will now be described with reference to the accompanying drawing, which shows the structure of a ready-made test body with sprayed layers incorporated by casting with the method according to the invention.

As seen the preferred embodiment of FIG. 1, two test pieces of the surface layer 10 attached to backing 11, which test pieces are to be examined, are mounted opposite to each other with a net of polymer material 12, preferably polytetraflouro ethylene, placed between the same, by one or several mounting clips 13. The purpose of the net on the one hand is to achieve a necessary distance between the two surface layers 10, so that they will not rub against each other during the casting, and on the other hand to absorb possible shrinking stresses, when the resin cures. Some surface layers can be incorporated by casting without the net.

In the present embodiment the test body 1 has a cylindrical form, and the test pieces are placed parallel with the longitudinal axis of said test body 1 on a fixed mutual distance.

The test pieces prepared in this way are then placed in a mould (not shown) which is placed in a vacuum chamber (not shown), and the air pressure is lowered to under 30 mbar. After waiting a predetermined period of time, preferably about 30 sec., the ready-mixed liquid casting resin of epoxy type, preferably Epoxy Pack 301 (obtainable from Logitech Ltd.), is poured into the mold with the test pieces, where air is let into the vacuum chamber to atmospheric pressure. Both of the porous surface layers 10 are, in this way, covered with casting resin of a type which will fill all pin-holes and voids in the same. Then, the mounted test pieces are lifted out of the mold and excess amount of epoxy is allowed to drip from the test pieces over the mold. This means that the amount of casting resin of epoxy type used in this embodiment will be reduced from about 18 g in the known cold moulding method to about 0.8 g.

Since the casting resin left in the mold has a curing time of several hours it can be used for several more test bodies.

The test pieces, from which the casting resin has dripped, are then placed in a known hot moulding press (Prontopress) and a suitable amount of pulverized phenolic plastic, preferably Phenolic Moulding Compound available from Perstorp AB, is filled into the press cavity, the lid of which is closed and the incorporation by casting is started in known manner, the test pieces being incorporated by casting under a pressure of about 5–15 kN and a temperature of about 150° C. to form the test body 1.

Due to the high temperature the casting resin of epoxy type cures very quickly and no formation of blisters will occur in the epoxy, probably due to the high surrounding pressure of about 5–15 kN. After about 15 minutes the test body is ready to be taken out.

The so produced test body I is then cut at one end at right angles to the longitudinal direction of the same for producing a circular end surface containing the surface layers 10 to be analyzed. The circular end surface is then lapped and the surface layers are analyzed and evaluated with the use of a microscope. Since the pin-holes and the voids in the porous surface layer now are filled with epoxy, a true structure is obtained.

The method according to the invention results in cost reductions, since the amount of casting resin of epoxy type is very low (about 0.8 g), and is more or less as fast as the known hot moulding method, but with the desired properties of the cold moulding method.

What is claimed is:

1. A prepared sample for the analysis of at least one sprayed porous surface layer, comprising:
   at least one sprayed porous surface layer attached to a backing;
   a net in contact with and covering said surface layer, wherein said net comprises a plurality of apertures;
   a first resin comprising a first plastic material that fills all pin-holes and voids in said surface layer and all of the apertures of said net; and
   wherein said at least one surface layer, said backing, said net and said first resin are encased by casting in a second resin comprising a second plastic material.

2. The prepared sample according to claim 1, wherein said porous sprayed surface layer comprises a thermally sprayed surface layer.

3. The prepared sample according to claim 1, wherein said porous sprayed surface layer has an edge that is analyzed.

4. The prepared sample according to claim 1, wherein the net is made of polytetraflouro ethylene.

5. The prepared sample according to claim 1, wherein said first plastic material is an epoxy resin.

6. The prepared sample according to claim 1, wherein said second plastic material is a phenolic resin.

* * * * *